United States Patent
Brasse et al.

(10) Patent No.: US 10,710,099 B2
(45) Date of Patent: *Jul. 14, 2020

(54) COMPOSITIONS AND METHODS FOR SELECTIVE SEPARATION OF MINERALS FROM SULFIDE ORES

(71) Applicant: Cytec Industries Inc., Princeton, NJ (US)

(72) Inventors: Mikael Brasse, White Plains, NY (US); Esau Arinaitwe, Norwalk, CT (US); Devarayasamudram Ramachandran Nagaraj, Stamford, CT (US)

(73) Assignee: Cytec Industries Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/513,043

(22) Filed: Jul. 16, 2019

(65) Prior Publication Data

US 2019/0336984 A1 Nov. 7, 2019

Related U.S. Application Data

(62) Division of application No. 15/726,810, filed on Oct. 6, 2017, now Pat. No. 10,369,577.

(60) Provisional application No. 62/405,514, filed on Oct. 7, 2016.

(51) Int. Cl.

| | |
|---|---|
| *B03D 1/016* | (2006.01) |
| *B03D 1/02* | (2006.01) |
| *B03D 1/01* | (2006.01) |
| *B03D 1/012* | (2006.01) |
| *C07C 333/14* | (2006.01) |
| *C08L 33/26* | (2006.01) |
| *B03D 1/008* | (2006.01) |

(52) U.S. Cl.
CPC .............. *B03D 1/02* (2013.01); *B03D 1/01* (2013.01); *B03D 1/012* (2013.01); *B03D 1/016* (2013.01); *C07C 333/14* (2013.01); *C08L 33/26* (2013.01); *B03D 1/008* (2013.01); *B03D 2201/005* (2013.01); *B03D 2201/007* (2013.01); *B03D 2201/02* (2013.01); *B03D 2201/04* (2013.01); *B03D 2201/06* (2013.01); *B03D 2203/02* (2013.01)

(58) Field of Classification Search
CPC .......... B03D 1/02; B03D 1/012; B03D 1/016; B03D 1/01; B03D 2201/005; B03D 2201/007; B03D 2201/02; B03D 2201/04; B03D 2201/06; B03D 1/008; B03D 2203/02; C07C 333/14; C08L 33/26
USPC ....................................................... 209/167
See application file for complete search history.

(56) References Cited

U.S. PATENT DOCUMENTS

| | | | |
|---|---|---|---|
| 4,196,073 A | 4/1980 | Gannon et al. | |
| 4,533,466 A | 8/1985 | Bresson et al. | |
| 4,554,068 A | 11/1985 | Kimble et al. | |
| 4,554,108 A | 11/1985 | Kimble et al. | |
| 4,622,131 A | 11/1986 | Bresson et al. | |
| 5,959,054 A | 9/1999 | Wang et al. | |
| 10,369,577 B2* | 8/2019 | Brasse | B03D 1/01 |
| 2015/0329486 A1 | 11/2015 | Daly | |

FOREIGN PATENT DOCUMENTS

| | | |
|---|---|---|
| CN | 103949351 A | 7/2014 |
| WO | 2015157498 A1 | 10/2015 |

OTHER PUBLICATIONS

International Search Report of PCT/US2017/055522; dated Jan. 19, 2018.
Written Opinion of PCT/US2017/055522; dated Jan. 19, 2018.
Valentine, W.M. et al., "Covalent cross-linking of proteins by carbon disulfide"; Chem Res. Toxicol.; 1992, vol. 5, No. 2; pp. 254-262.

* cited by examiner

*Primary Examiner* — Thomas M Lithgow
(74) *Attorney, Agent, or Firm* — Charles E. Bell, Esq.

(57) ABSTRACT

Compositions including blends of one or more acrylamide/allyl thiourea polymer as a first depressant, and one or more carboxyalkyl dithiocarbamate compound as a second depressant, and their use as depressants in the beneficiation of sulfide minerals from ores and/or concentrates are disclosed herein, along with methods for selectively separating value sulfide minerals from non-value sulfide minerals in a froth flotation process for the recovery of such value minerals.

20 Claims, No Drawings

COMPOSITIONS AND METHODS FOR SELECTIVE SEPARATION OF MINERALS FROM SULFIDE ORES

CROSS-REFERENCE TO RELATED APPLICATIONS

This application is a divisional of U.S. application Ser. No. 15/726,810, filed Oct. 6, 2017 (now U.S. Pat. No. 10,369,577 issued Aug. 6, 2019), which claims benefit of priority to U.S. Provisional Application No. 62/405,514, filed Oct. 7, 2016 (expired), each of which is incorporated herein by reference in its entirety.

BACKGROUND OF THE INVENTION

1. Field of the Invention

The present invention generally relates to reagents and processes for recovering minerals from mineral ore bodies or concentrates through selective separation of such minerals. More particularly, the present invention relates to mineral depressant compositions useful in beneficiating minerals from sulfide ore bodies or concentrates by froth flotation processes.

2. Description of the Related Art

Complex sulfide ores are an important source of many base metals and precious metals, and it is quite common to find 3-5 types of metals in a single ore deposit, in addition to several types of impurity elements. The main objective for treating complex sulfide ores is maximum recovery of value metals and precious metals (if any), and minimum contamination of the value sulfide concentrate by non-value sulfide minerals. While treatment methods depend on the relative proportions of the different metals, bulk flotation of sulfides followed by separation of value sulfides and differential flotation of sulfides is a primary beneficiating method.

Thus, flotation processes used for recovery and/or concentrating value minerals (i.e., desired minerals) from ores are well known in the field, and can be generally summarized to include crushing and grinding the mineral containing ore to obtain a pulp, and adding one or more various additives/reagents such as mineral flotation or collector agents, frothers, suppressants/depressants, stabilizers, modifiers, etc., to at least one stage of the process to assist in selectively separating the value minerals from the non-value (i.e., undesirable or gangue) minerals of the ores.

Depressants have been particularly effective for making sulfide collectors more selective for value sulfide minerals, and thereby improving the flotation separation of value sulfides. Depressant reagents selectively prevent or inhibit adsorption of the collectors on certain of the mineral particles surfaces present in the flotation slurry/pulp. The non-value sulfide minerals and gangue minerals are thereby 'depressed' to reduce the levels of non-value sulfide contaminants reporting to the concentrators. The mineral pulp can then be aerated to produce a froth at the surface. Those minerals that adhere to the bubbles or froth are skimmed or otherwise removed, and the mineral-bearing froth is collected and further processed to obtain the value minerals.

Various froth flotation processes and reagents have been detailed in the prior art. For example, U.S. Pat. No. 4,533,466 to Bresson et al. discloses mercaptopolycarboxylic acids such as the trithiocarbonate derivates thereof and alkali metal salts as depressants useful in improving molybdenum flotation processes, wherein less iron, copper, and lead are present in the molybdenum values removed (i.e., copper, iron and lead values are depressed and molybdenite is floated).

U.S. Pat. No. 4,554,068 to Kimble et al. discloses carboxyalkyl dithiocarbamates with N-substitutions as depressants useful in flotation reagents of certain metal sulfide minerals based on copper, nickel, iron, lead, and zinc.

U.S. Pat. No. 4,622,131 to Bresson et al. discloses an amino-substituted carboxylic acid derivative or a mercapto-substituted carboxylic acid derivative in combination with a thiocarbonate derivative as a minerals depressant for the recovery of copper values from a copper-containing ore.

The majority of prior art sulfide depressants have been generally selected from highly toxic and difficult to handle inorganic compounds such as sodium cyanide, (NaCN), sodium hydrosulfide, (NaSH), and Nokes reagent ($P_2S_5$+ NaOH). These conventional sulfide depressants possess a number of serious problems and shortcomings accompanying their use. For example, such depressants are extremely toxic and pose potential hazards in terms of safety, health, storage, and transportation. The preparation and use of these reagents requires special (and costly) safety procedures to avoid toxic $H_2S$ gas. Additionally, an offensive stench is attendant to these depressants, which is a huge concern for flotation cell operators and nearby communities. They cannot be used safely over a wide range of pH values, but instead must be used at high pH values. Consequently, lime consumption is consequently increased along with reagent costs.

Moreover, the conventional inorganic depressants are often either nonselective or, when used in sufficient quantities to provide good separation, provide economically unsatisfactory concentrates, i.e., the yield of value minerals is too low. Accordingly, the cost-effectiveness of these inorganic reagents is inadequate due to their high treatment costs.

Other prior art depressants have been successfully used to reduce the high consumption of inorganic reagents and, therefore, lessen the safety and health concerns associated with the use of large amounts of such hazardous depressants. For example, U.S. Pat. No. 4,888,106 to Lipp and Nagaraj, and U.S. Pat. No. 4,966,938 to Wang and Nagaraj, disclose a low molecular weight, water soluble polymer having an allyl thiourea functional group and a hydrophilic acrylamide group (commercialized as AERO® 7260 HFP by Cytec Industries Inc., Woodland Park, N.J.), which can be used in conjunction with a small amount of NaSH. As disclosed, the combination of AERO® 7260 and NaSH at very small dosages (typically $1/10^{th}$ to $1/30^{th}$ of the total NaSH consumption typically used) effectively reduces up to 80% of the NaSH used in the circuit or plant. In practice, however, NaSH reduction is only about 60%. Thus, even with the use of AERO® 7260 HFP the reduced amounts of NaSH still possess serious safety and health concerns.

While most of the performance deficiencies, including insufficient depression of gangue sulfide minerals associated with the use of inorganic depressants such as NaSH, $Na_2S$, or Nokes, are solved with the use of AERO® 7260 HFP, these inorganic depressants cannot be blended with AERO® 7260 HFP to produce one chemically stable product. Thus, flotation operators are faced with the difficulty of separately dosing the two depressants. Currently AERO® 7260 HFP is not blended with any other chemical. The challenge that arises from co-dosing is that the inorganic depressant requires careful monitoring of the pulp potential while the AERO® 7260 HFP requires judicious use of small amounts to achieve adequate depression of non-value sulfide minerals while maintaining value mineral flotation.

Accordingly, establishing appropriate dosages of the inorganic depressant and AERO® 7260 HFP is a huge challenge facing operators. Common consequences resulting from the difficulty of establishing appropriate NaSH and AERO® 7260 HFP dosages are overuse of NaSH which reduces the amount of NaSH replaced by AERO® 7260 HFP and/or overdosing of AERO® 7260 HFP which retards value mineral flotation and reduces the value mineral concentrate yield.

Therefore, there is still a need in the art for a reagent system that substantially reduces and/or completely eliminates the consumption of hazardous organic depressants as well as selectively depresses non-value and gangue sulfide minerals to concurrently maintain a high content of value sulfide minerals and/or precious metal minerals in the concentrates. Furthermore, a safe, practical, and sustainable depressant system that is chemically stable, can be applied over a wide dosage range at lower pH that those currently available in the prior art, and which is available as a one-pack product would be a useful advance in the art and could find rapid acceptance in the industry.

SUMMARY OF THE INVENTION

The foregoing and additional objects are attained in accordance with the principles of the invention wherein the inventors describe herewith for the first time an environmentally friendly reagent system for use as a depressant in a froth flotation process for recovery of value sulfide minerals from ores/concentrates containing complex sulfide minerals. This new reagent system is physically and chemically stable (i.e., no hydrolysis at different pH and no reactions leading to degradation of product), can be blended as an aqueous one-pack product, provides improved selectivity for non-value minerals over prior art reagent systems currently in use, and can be used without potentially harmful inorganic depressants such as NaSH, $Na_2S$, or Nokes.

Accordingly, in one aspect the invention provides compositions of matter being a blend of a first depressant and a second depressant, wherein the first depressant is a polymer having a weight average molecular weight from 1,000 g/mol to 1,000,000 g/mol including:

i) X units of an acrylamide derivative according to Formula (I):

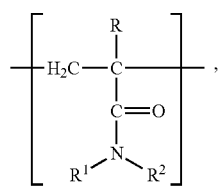

wherein
each of R, $R^1$, and $R^2$ is independently chosen from H, $C_1$-$C_4$ alkyl, or $C_6$-$C_{12}$ aryl; and
X is a residual mole percent fraction by weight based on the total mole percent by weight of Y and Z;

ii) Y units of a thiourea derivative according to Formula (II):

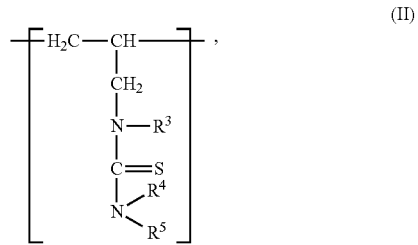

wherein
$R^3$ is chosen from H, a $C_1$-$C_4$ alkyl, or $C_6$-$C_{12}$ aryl;
each of $R^4$ and $R^5$ is independently chosen from H, $C_1$-$C_4$ hydrocarbyl, or a $C_6$-$C_{12}$ aryl; and
Y is a mole percent fraction from 1% to 50% by weight based on the total weight of X, Y, and Z; and iii) Z units of a polymerization residue of any monomer copolymerizable with the derivatives according to Formulas (I) and (II), wherein Z is a mole percent fraction from 0% to 50% by weight based on the total weight of X, Y, and Z; and wherein the second depressant is a dithiocarbamate compound according to Formula (III):

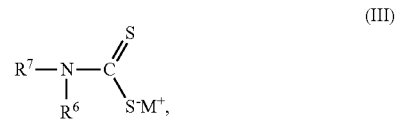

wherein
$R^6$ is chosen from H, or a moiety having from 1-12 carbon atoms and one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl;
$R^7$ is chosen from a moiety having from 1-12 carbon atoms and one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl;
each instance of M is independently chosen from a cation selected from the group consisting of alkali metal, metal, or $R^{10}_4N^+$, wherein each instance of $R^{10}$ is independently chosen from H or a $C_1$-$C_{12}$ alkyl, and wherein the blend is further characterized as being an aqueous solution; and having 4<pH≤14 at a temperature from −5° C. to 85° C.

Similarly, in a second aspect, the invention provides use of the composition and/or methods for selectively separating value sulfide minerals from non-value sulfide minerals in a froth flotation process for recovering said value minerals from an ore or concentrate containing said value and non-value minerals, by:

adding to one or more stage of the froth flotation process a first depressant and a second depressant in an amount sufficient to increase the value minerals in the froth, thereby selectively separating the value minerals from the non-value minerals, wherein the first depressant is a polymer having a weight average molecular weight from 1,000 g/mol to 1,000,000 g/mol including:

i) X units of an acrylamide derivative according to Formula (I):

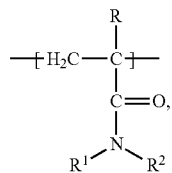

wherein
each of R, $R^1$, and $R^2$ is independently chosen from H, $C_1$-$C_4$ alkyl, or $C_6$-$C_{12}$ aryl; and
X is a residual mole percent fraction by weight based on the total mole percent by weight of Y and Z;

ii) Y units of a thiourea derivative according to Formula (II):

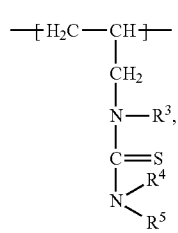

wherein
$R^3$ is chosen from H, a $C_1$-$C_4$ alkyl, or $C_6$-$C_{12}$ aryl;
each of $R^4$ and $R^5$ is independently chosen from H, $C_1$-$C_4$ hydrocarbyl, or a $C_6$-$C_{12}$ aryl; and
Y is a mole percent fraction from 1% to 50% by weight based on the total weight of X, Y, and Z; and iii) Z units of a polymerization residue of any monomer copolymerizable with the derivatives according to Formulas (I) and (II), wherein Z is a mole percent fraction from 0% to 50% by weight based on the total weight of X, Y, and Z; and
wherein the second depressant is a dithiocarbamate compound according to Formula (III):

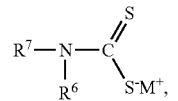

wherein
$R^6$ is chosen from H, or a moiety having from 1-12 carbon atoms and one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl;
$R^7$ is chosen from a moiety having from 1-12 carbon atoms and one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl; and
each instance of M is independently chosen from a cation selected from the group consisting of alkali metal, metal, or $R^{10}_4N^+$, wherein each instance of $R^{10}$ is independently chosen from H or a $C_1$-$C_{12}$ alkyl.

These and other objects, features and advantages of this invention will become apparent from the following detailed description of the various aspects of the invention taken in conjunction with the accompanying Examples.

DETAILED DESCRIPTION OF CERTAIN EMBODIMENTS OF THE INVENTION

As summarized above, the present invention is based at least in part on the discovery of a new depressant reagent system containing a first depressant having at least one low molecular weight polymer and a second depressant having at least one carboxyalkyl dithiocarbamate. The first depressant that is a low molecular weight polymer can be characterized as the copolymerization product of an allyl thiourea with an acrylamide. The second depressant that is a carboxyalkyl dithiocarbamate can be characterized as having a first portion that is of low molecular weight and includes the dithiocarbamate functional group, and a second portion that includes a hydrophilic carboxylate group. While each of the first and second depressant are known individually as being generally useful as a depressant in froth flotation processes for separation of metal sulfide minerals, neither provides satisfactory performance or is dosage efficient when used individually.

Accordingly, the inventors have surprisingly discovered that the first depressant and the second depressant can be used together to provide unexpected and/or superior performance in selective separation of value minerals from non-value minerals (e.g., by depressing non-value minerals and/or gangue minerals thereby increasing the value minerals in the concentrates), and at significantly lower dosage, than can be achieved by using either of the depressants alone or by using currently available conventional depressants. Additionally, the first and second depressant can be blended as described herein to produce a composition that is chemically and physically stable and safer to use under operating conditions common in froth flotation processes involving metal sulfide ores. Such blended compositions can be provided for simple dosing as a one-pack blend. However, as those skilled in the art will appreciate the first and second depressant can also be co-dosed separately.

Although certain embodiments of the invention contemplate that the first and second depressant can also be co-dosed with such commonly used inorganic depressants such as NaSH, $N_2S$, and Nokes, the use with such depressants is optional and the dosage amount of inorganic depressant is advantageously reduced. Therefore, the depressant compositions according to the invention as described and claimed herein do not present the health, safety, and environmental concerns of the inorganic depressants commonly used, and they do not generate toxic gases such as $H_2S$ and $CS_2$ under froth flotation conditions, or upon prolonged storage.

As those skilled in the art will appreciate, the depressant compositions described herein can also be used in conjunction with other common flotation reagents such as frothers, collectors, modifiers, pH regulators, etc., and are effective in a wide range of pH.

As employed throughout the disclosure of the invention, the following terms are provided to assist the reader. Unless otherwise defined, all terms of art, notations and other scientific or industrial terms or terminology used herein are intended to have the meanings commonly understood by those of skill in the chemical arts. In some cases, terms with commonly understood meanings are defined herein for clarity and/or for ready reference, and the inclusion of such definitions herein should not necessarily be construed to represent a substantial difference over the definition of the term as generally understood in the art unless otherwise indicated. As used herein and in the appended claims, the singular forms include plural referents unless the context clearly dictates otherwise. Throughout this specification, the terms retain their definitions.

In general, ores contain, inter alia, both "value" and "non-value" minerals. In this context, the term "value" mineral refers to the metal(s) (base or precious) or mineral(s) that are the primary object of the flotation process, i.e., the metal or mineral ore or concentrate from which it is desirable to remove impurities. The term "non-value" mineral refers to the metal(s) or mineral(s) for which removal from the value mineral is desired, i.e., impurities in the value mineral. A non-value mineral is not necessarily discarded, and may be considered a value mineral in a subsequent process.

"Effective amount" means the dosage of any reagents on an active basis (such as the depressant compositions described herein) necessary to provide the desired performance in the system or circuit being treated (such as the depression or rejection of non-sulfide gangue minerals and/or non-value metal sulfides) when compared to an untreated control system or system using a reagent product of the prior art.

As used herein, the term "acrylamide derivative" or "thiourea derivative" refers to compounds having a functional acrylamide or thiourea moiety, respectively, in the compound.

The term "hydrocarbyl" as used herein is a generic term encompassing aliphatic, alicyclic and aromatic groups or radicals having an all-carbon backbone and consisting of carbon and hydrogen atoms. Examples of hydrocarbyl groups include alkyl, cycloalkyl, cycloalkenyl, carbocyclic aryl (aryl), alkenyl, alkynyl, alkylcycloalkyl, cycloalkylalkyl, cycloalkenylalkyl, and carbocyclic aralkyl, alkaryl, aralkenyl and aralkynyl groups.

Generally, and by way of example, the hydrocarbyl groups can have up to 36 carbon atoms, unless the context requires otherwise. Hydrocarbyl groups with from 1 to 24 carbon atoms are preferred, with 1 to 12 carbons more preferred. Within the sub-set of hydrocarbyl groups, particular examples are $C_{1-4}$ hydrocarbyl groups, $C_{1-12}$ hydrocarbyl groups, or $C_{1-10}$ hydrocarbyl groups, although any individual value, range, or combination of values selected from $C_1$ through $C_{36}$ hydrocarbyl groups is contemplated by the inventors as if specifically recited herein.

As indicated by the context used herein, the term "alkyl" is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl, pentyl, hexyl, or cyclohexyl and the like. Preferred alkyl groups include those of $C_{12}$ or below.

The term "aryl" as used herein refers to cyclic aromatic hydrocarbons that do not contain heteroatoms in the ring. In any or all embodiments, aryl groups contain about 6 to about 14 carbons in the ring portions of the groups. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those known to persons of skill in the art.

The terms "comprised of," "comprising," or "comprises" as used herein includes embodiments "consisting essentially of" or "consisting of" the listed elements.

Those skilled in the art will appreciate that while preferred embodiments are discussed in more detail below, multiple embodiments of the depressant reagent system described herein are contemplated as being within the scope of the present invention. Thus, it should be noted that any feature described with respect to one aspect or one embodiment of the invention is interchangeable with another aspect or embodiment of the invention unless otherwise stated.

Furthermore, for purposes of describing the present invention, where an element, component, or feature is said to be included in and/or selected from a list of recited elements, components, or features, those skilled in the art will appreciate that in the related embodiments of the invention described herein, the element, component, or feature can also be any one of the individual recited elements, components, or features, or can also be selected from a group consisting of any two or more of the explicitly listed elements, components, or features. Additionally, any element, component, or feature recited in such a list may also be omitted from such list.

Those skilled in the art will further understand that any recitation herein of a numerical range by endpoints includes all numbers subsumed within the recited range (including fractions), whether explicitly recited or not, as well as the endpoints of the range and equivalents. The term "et seq." is sometimes used to denote the numbers subsumed within the recited range without explicitly reciting all the numbers. Disclosure of a narrower range or more specific group in addition to a broader range or larger group is not a disclaimer of the broader range or larger group.

Accordingly, in one aspect the invention provides compositions of matter useful as depressant reagent systems including a blend of a first depressant and a second depressant.

wherein the first depressant is a polymer having a weight average molecular weight from 1,000 g/mol to 1,000,000 g/mol comprising:

i) X units of an acrylamide derivative according to Formula (I):

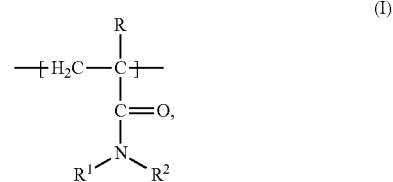

wherein
    each of R, $R^1$, and $R^2$ is independently chosen from H, $C_1$-$C_4$ alkyl, or $C_6$-$C_{12}$ aryl; and
    X is a residual mole percent fraction by weight based on the total mole percent by weight of Y and Z;

ii) Y units of a thiourea derivative according to Formula (II):

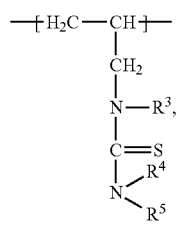

wherein
R$^3$ is chosen from H, a C$_1$-C$_4$ alkyl, or C$_6$-C$_{12}$ aryl;
each of R$^4$ and R$^5$ is independently chosen from H, C$_1$-C$_4$ hydrocarbyl, or a C$_6$-C$_{12}$ aryl; and
Y is a mole percent fraction from 1% to 50% by weight based on the total weight of X, Y, and Z; and
iii) Z units of a polymerization residue of any monomer copolymerizable with the derivatives according to Formulas (I) and (II), wherein Z is a mole percent fraction from 0% to 50% by weight based on the total weight of X, Y, and Z; and
wherein the second depressant is a dithiocarbamate compound according to Formula (III):

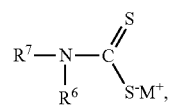

wherein
R$^6$ is chosen from H, or a moiety having from 1-12 carbon atoms and one or more functional groups selected from OH, SO$_3^-$M$^+$, COO$^-$M$^+$, and CONR$^8$R$^9$, wherein each of R$^8$ and R$^9$ is independently chosen from H or C$_1$-C$_4$ alkyl;
R$^7$ is chosen from a moiety having from 1-12 carbon atoms and one or more functional groups selected from OH, SO$_3^-$M$^+$, COO$^-$M$^+$, and CONR$^8$R$^9$, wherein each of R$^8$ and R$^9$ is independently chosen from H or C$_1$-C$_4$ alkyl;
each instance of M is independently chosen from a cation selected from the group consisting of alkali metal, metal, or R$^{10}_4$N$^+$, wherein each instance of R$^{10}$ is independently chosen from H or a C$_1$-C$_{12}$ alkyl, and
wherein the blend is further characterized as being an aqueous solution; and having 4<pH<14 at a temperature from −5° C. to 85° C.

Polymers of the first depressant are generally known from U.S. Pat. No. 4,888,106, to Lipp and Nagaraj, and may be prepared by routine polymerization techniques known to those skilled in the art, wherein X units of the acrylamide derivative according to Formula (I) is copolymerized with Y units of the thiourea derivative according to Formula (II) and, optionally, with comonomer unit Z. In any or all embodiments, the acrylamide derivative according to Formula (I) includes, but is not limited to, those derived from acrylamide per se, alkyl acrylamides such as methacrylamide, etc. and N-substituted acrylamide and methacrylamides such as N,N'-dimethylacrylamide.

In any or all embodiments, the first depressant is AERO® 7260 HFP (available from Cytec Industries Inc., Woodland Park, N.J.).

In the same or alternate embodiments, the thiourea derivative according to Formula (II) includes, but is not limited to, allyl thiourea; N-allyl-N'-methyl thiourea; N-allyl-N'-benzoyl thiourea; and N-allyl-N-methyl-N',N'-dimethyl thiourea.

In still the same or alternate embodiments, the (Z) units of the polymers of the first depressant defined above generally include, but are not limited to, monomers such as acrylonitrile, styrene, cationics (such as diallyl dimethyl ammonium chloride, methacrylamidopropyl trimethylammonium chloride, acrylamidopropyl trimethylammonium chloride, dimethylaminopropyl methacrylamide, dimethylaminoethyl acrylate or methacrylate, or their quaternary salts), acrylic, methacrylic or maleic acids, their alkali metal (e.g., sodium or potassium, or ammonium) salts, and alkyl esters thereof, and the like.

Carboxyalkyl dithiocarbamates compounds of the second depressant are generally known from U.S. Pat. No. 4,554,068 to Kimble et al., and can include, for example, one or more of the following:
disodium N-carboxymethyl dithiocarbamate;
disodium N-1-carboxyethyl dithiocarbamate;
disodium N-1-carboxypropyl dithiocarbamate;
disodium N-1-carboxybutyl dithiocarbamate;
disodium (N-carboxymethyl-N-methyl) dithiocarbamate;
disodium (N-1-carboxyethyl-N-methyl) dithiocarbamate;
disodium (N-1-carboxypropyl-N-methyl) dithiocarbamate;
disodium (N-1-carboxybutyl-N-methyl) dithiocarbamate;
disodium (N-carboxymethyl-N-ethyl) dithiocarbamate;
disodium (N-1-carboxyethyl-N-ethyl) dithiocarbamate;
disodium (N-1-carboxypropyl-N-ethyl) dithiocarbamate;
disodium (N-1-carboxybutyl-N-ethyl) dithiocarbamate;
dipotassium N-carboxymethyl dithiocarbamate;
dipotassium N-1-carboxyethyl dithiocarbamate;
dipotassium N-1-carboxybutyl dithiocarbamate;
dilithium N-carboxymethyl dithiocarbamate;
dilithium N-1-carboxyethyl dithiocarbamate; and
dilithium N-1-carboxypropyl dithiocarbamate.

In any or all embodiments, the second depressant is the dipotassium salt of carboxymethyl dithiocarbamate ("CDTC") (dipotassium N-carboxymethyl dithiocarbamate).

The depressant compositions are compatible with various other flotation reagents known to those skilled in the art including, for example, frothers, modifiers, dispersants, pH regulators, surface modifying agents, activators, collectors, stabilizers, depressants, or any combination of two or more of these reagents. Accordingly, any or all of the embodiments of the depressant composition disclosed herein can include any one or more of such flotation reagents.

In another aspect, the invention provides methods for selectively separating value sulfide minerals from non-value sulfide minerals in a froth flotation process for the recovery of said value minerals from an ore or concentrate containing said value and non-value minerals, by adding to one or more stage of the froth flotation process a first depressant and a second depressant in an amount sufficient (i.e., an effective amount) to increase the value minerals in the froth, thereby selectively separating the value minerals from the non-value minerals. The first depressant and second depressant are as previously described herein.

While it is generally believed that the blend of first and second depressant compositions disclosed herein are useful for suppressing or depressing the flotation of certain metal sulfide minerals during ore flotation processes, it will also be understood to those skilled in the art that the depressant composition described herein may suppress a mixture of metals or minerals contained in a particular mining deposit, ore, or concentrate, which mixture can be further separated by subsequent froth flotations or any other conventional separating methods. Any or all of the depressant compositions disclosed herein are particularly useful for suppressing minerals based on sulfides of copper, nickel, iron, lead, zinc, or molybdenum, or complex ores/concentrates containing mixtures of any two or more of these. Accordingly, any or all of the processes of the present invention are directed to the separation of sulfides including, but not limited to, gangue sulfides from copper ores, copper-molybdenum ores, complex sulfide ores (containing lead, copper, zinc, silver, gold), nickel and nickel-cobalt ores, gold ores, or gold-silver ores.

As those skilled in the art will appreciate, in any or all embodiments of the invention the first and second depressant can be co-dosed in the froth flotation process in any manner known in the art, i.e., simultaneously, sequentially. In the same or alternate embodiments, the first and second depressant can be blended prior to addition, by any manner known to those in the art or by the methods described herein, and dosed together such as by a one-pack blend.

Those skilled in the art will further appreciate that the dosage amount of first and second depressant composition may depend on a variety of factors such as whether the pulp is from an ore or a concentrate, or whether there is a large or small amount of non-value mineral to be depressed, or even the overall mineral contents. Accordingly, in any or all of the embodiments described herein the dosing schedule of a blend of the first and second depressant can be from 2 kg/ton, et. seq. to 15 kg/ton of ore or concentrate.

In the same or alternative embodiments, the first depressant and the second depressant can be co-dosed. In any or all embodiments where co-dosing is utilized, the dosing schedule of the first depressant can be from 0.5 kg/ton, et. seq. to 1.5 kg/ton of ore or concentrate. In the same or alternate embodiments, the dosing schedule of the second depressant can be at least 1.5 kg/ton of ore or concentrate. That is to say that there really is no upper limit on the amount of second depressant in a co-dosing scenario. In any or all embodiments, the dosing schedule of the second depressant in a co-dosing scenario can be up to 25 kg/ton of ore or concentrate; preferably up to 15 kg/ton of ore or concentrate; and more preferably up to 10 kg/ton of ore or concentrate. In a preferred embodiment, the dosing schedule of the second depressant can be from 1.5 kg/ton, et. seq. to 7.5 kg/ton of ore or concentrate.

The invention as fully described herein includes at least the following embodiments:

Embodiment 1. A composition of matter comprising a blend of a first depressant and a second depressant,
wherein the first depressant is a polymer having a weight average molecular weight from 1,000 g/mol to 1,000,000 g/mol comprising:

i) X units of an acrylamide derivative according to Formula (I):

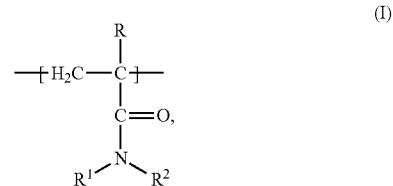

wherein
each of R, $R^1$, and $R^2$ is independently chosen from H, $C_1$-$C_4$ alkyl, or $C_6$-$C_{12}$ aryl; and
X is a residual mole percent fraction by weight based on the total mole percent by weight of Y and Z;

ii) Y units of a thiourea derivative according to Formula (II):

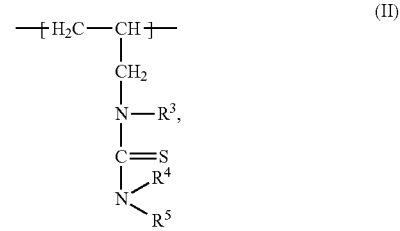

wherein
$R^3$ is chosen from H, a $C_1$-$C_4$ alkyl, or $C_6$-$C_{12}$ aryl;
each of $R^4$ and $R^5$ is independently chosen from H, $C_1$-$C_4$ hydrocarbyl, or a $C_6$-$C_{12}$ aryl; and
Y is a mole percent fraction from 1% to 50% by weight based on the total weight of X, Y, and Z; and iii) Z units of a polymerization residue of any monomer copolymerizable with the derivatives according to Formulas (I) and (II), wherein Z is a mole percent fraction from 0% to 50% by weight based on the total weight of X, Y, and Z; and
wherein the second depressant is a dithiocarbamate compound according to Formula (III):

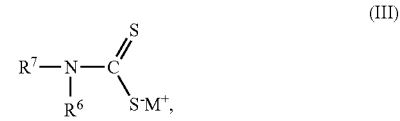

wherein
$R^6$ is chosen from H, or a moiety having from 1-12 carbon atoms and one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl;
$R^7$ is chosen from a moiety having from 1-12 carbon atoms and one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl;
each instance of M is independently chosen from a cation selected from the group consisting of alkali metal, metal, or $R^{10}_4N^+$, wherein each instance of $R^{10}$ is independently chosen from H or a $C_1$-$C_{12}$ alkyl, wherein the blend is further characterized as being an aqueous solution; and having
$4 < pH < 14$ at a temperature from $-5°$ C. to $85°$ C.

Embodiment 2. A composition according to embodiment 1, wherein the first depressant and the second depressant are present at a weight ratio in a range from 20:80 to 80:20.

Embodiment 3. A composition according to embodiment 2, wherein the weight ratio of the first depressant to the second depressant is from 25:75 to 50:50.

Embodiment 4. A composition according to any one of embodiments 1 to 3, wherein said blend of the first and second depressant is from 10 to 50 parts by weight, per 100 parts by weight of water, and having $4 < pH \leq 14$ at a temperature from $20°$ C. to $50°$ C.

Embodiment 5. A composition according to any one of embodiments 1 to 4, wherein each of R, $R^1$, $R^2$, $R^3$, $R^4$, and $R^5$ is H.

Embodiment 6. A composition according to any one of embodiments 1 to 5, wherein said first depressant has a weight average molecular weight from 10,000 g/mol to 100,000 g/mol.

Embodiment 7. A composition according to any one of embodiments 1 to 6, wherein X units of Formula (I) to Y units of Formula (II) is present at a weight ratio in a range from 10:90 to 95:5.

Embodiment 8. A composition according to embodiment 7, wherein X units of Formula (I) is greater than 50% and no Z units are present.

Embodiment 9. A composition according to any one of the preceding embodiments, wherein $R^6$ is H, $R^7$ is $CH_2COO^- M^+$, and each $M^+$ in Formula (III) is K.

Embodiment 10. A composition according to any one of embodiments 1 to 9, wherein the blend of the first and second depressant further comprises, or is used in combination with, a value mineral enhancing amount of a surface modifying agent.

Embodiment 11. A composition according to embodiment 10, wherein the surface modifying agent is one or more compound selected from the group consisting of NaSH, NaCN, Nokes reagent, mercapto ethanol, thioglycolic acid or salts thereof (including sodium, potassium, calcium, magnesium, or aluminum salts), sodium ferrocyanides, potassium ferrocyanides, hydroxyethyl trithiocarbonates, carboxyethyl trithiocarbonates, sodium trithiocarbonates, hydrogen peroxide, ozone, air, oxygen, sulfur dioxide, zinc cyanide, calcium cyanide, arsenic Nokes, mercapto propionic acid, mercapto succinic acid, 2-thiouracil, and thioglycerol.

Embodiment 12. A composition according to embodiment 10 or embodiment 11, wherein the surface modifying agent is NaSH, Na2S, sodium salt of thioglycolic acid, or Nokes reagent and is present from 0.5 wt. % to 99.5 wt. %, based on the total weight of the blend.

Embodiment 13. A method for selectively separating value sulfide minerals from non-value sulfide minerals in a froth flotation process for the recovery of said value minerals from an ore or concentrate containing said value and non-value minerals, the method comprising:
adding to one or more stage of the froth flotation process a first depressant and a second depressant in an amount sufficient to increase the value minerals in the froth, thereby selectively separating the value minerals from the non-value minerals,
wherein the first depressant is a polymer having a weight average molecular weight from 1,000 g/mol to 1,000,000 g/mol comprising:

i) X units of an acrylamide derivative according to Formula (I):

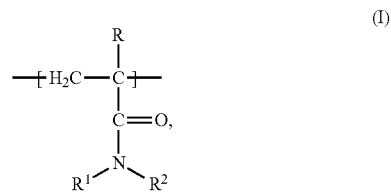

wherein
each of R, $R^1$, and $R^2$ is independently chosen from H, $C_1$-$C_4$ alkyl, or $C_6$-$C_{12}$ aryl; and
X is a residual mole percent fraction by weight based on the total mole percent by weight of Y and Z;

ii) Y units of a thiourea derivative according to Formula (II):

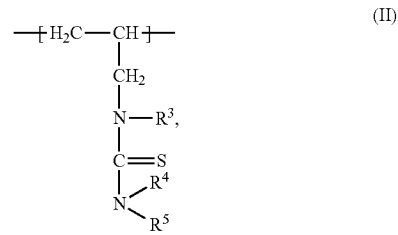

wherein
$R^3$ is chosen from H, a $C_1$-$C_4$ alkyl, or $C_6$-$C_{12}$ aryl;
each of $R^4$ and $R^5$ is independently chosen from H, $C_1$-$C_4$ hydrocarbyl, or a $C_6$-$C_{12}$ aryl; and
Y is a mole percent fraction from 1% to 50% by weight based on the total weight of X, Y, and Z; and iii) Z units of a polymerization residue of any monomer copolymerizable with the derivatives according to Formulas (I) and (II), wherein Z is a mole percent fraction from 0% to 50% by weight based on the total weight of X, Y, and Z; and
wherein the second depressant is a dithiocarbamate compound according to Formula (III):

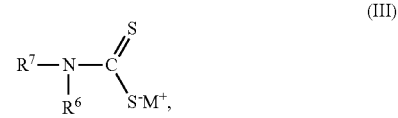

wherein
$R^6$ is chosen from H, or a moiety having from 1-12 carbon atoms and one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl;
$R^7$ is chosen from a moiety having from 1-12 carbon atoms and one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl;
each instance of M is independently chosen from a cation selected from the group consisting of alkali metal, metal, or $R^{10}{}_4N^+$, wherein each instance of $R^{10}$ is independently chosen from H or a $C_1$-$C_{12}$ alkyl.

Embodiment 14. A method according to embodiment 13, wherein the first and second depressant are added as a one pack blend.

Embodiment 15. A method according to embodiment 13 or embodiment 14, wherein the first and second depressant are as defined in any one of embodiments 2-12.

Embodiment 16. A method according to any one of embodiments 13 to 15 further comprising adding an effective amount of one or more flotation reagents selected from the group consisting of collectors, frothers, froth phase modifiers, dispersants, depressants, suppressants, pH regulators, and activators to one or more stages of said froth flotation process.

Embodiment 17. A method according to any one of embodiments 13 to 16 further comprising recovering said value minerals from the froth.

18. A method according to any one of embodiments 13 to 17, wherein the first and second depressant are added together in a one pack blend in a dosage of 2 kg/ton to 15 kg/ton of ore or concentrate; or wherein the first and second depressant are co-dosed and the dosage of the first depressant is from 0.5 kg/ton to 1.5 kg/ton of ore or concentrate, and the dosage of the second depressant is from 1.5 kg/ton to 25 kg/ton (preferably to 20 kg/ton, 15 kg/ton, 10 kg/ton, or 7.5 kg/ton) of ore or concentrate.

Embodiment 19. A method according to any one of embodiments 13 to 18, wherein said value minerals are selected from the group consisting of sulfides of molybdenum, copper, zinc, nickel, lead, and mixtures thereof.

Embodiment 20. A method according to embodiment 19, wherein said value mineral is molybdenite and said non-value mineral is copper sulfides and/or iron sulfides.

Embodiment 21. Use of a composition of matter according to any one of embodiments 1 to 12 for use as a depressant in a froth flotation process for recovery of value sulfide minerals from ores/concentrates containing complex sulfide minerals, preferably administered as an aqueous one-pack product without harmful inorganic depressants such as NaSH, $Na_2S$, or Nokes.

EXAMPLES

The following examples are provided to assist one skilled in the art to further understand certain embodiments of the present invention. These examples are intended for illustration purposes and are not to be construed as limiting the scope of the various embodiments of the present invention.

Example 1—Synthesis of Various Dithiocarbamate Compounds

Various dithiocarbamate compounds according to Formula (III):

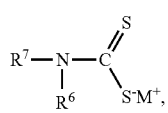

(III)

were prepared according to the methods outlined below. A summary of analogs is provided in Table 1.

TABLE 1

Dithiocarbamate analogues.

| Amine | Name | R7 | R6 | M |
|---|---|---|---|---|
| Glycine | CDTC | $MO_2CCH_2$ | H | K |
| Sarcosine | SDTC | $MO_2CCH_2$ | $CH_3$ | K |
| Taurine | TDTC | $MO_3SCH_2CH_2$ | H | K |
| Iminodiacetic acid | IDTC | $MO_2CCH_2$ | $MO_2CCH_2$ | K |
| Beta-Alanine | BDTC | $MO_2C(CH_2)_2$ | H | K |
| γ-Aminobutyric acid | ADTC | $MO_2C(CH_2)_3$ | H | K |
| L-glutamic acid | GDTC | $MO_2C(CH_2)_2$ $CH(CO_2M)$ | H | K |
| Ethanolamine | EDTC | $HO(CH_2)_2$ | H | $HNEt_3$ |
| Diethanolamine | DDTC | $HO(CH_2)_2$ | $HO(CH_2)_2$ | $HNEt_3$ |
| 3-amino-1-propanol | PDTC | $HO(CH_2)_3$ | H | $HNEt_3$ |
| Diethanolamine | KDTC | $HO(CH_2)_2$ | $HO(CH_2)_2$ | K |

The most common route to make alkyl dithiocarbamates uses an amine, CS2 and a base, amine or hydroxide salt, as raw materials with a suitable solvent e.g. water, alcohol or diethyl ether as shown in the literature, such as Thorn, G. D.; Ludwig, R. A. *The Dithiocarbamates and Related Compounds*; Elsevier: New York, 1962. Kimble, K. B.; Mark, H. W.; Bresson, C. R. "i Alkali carboxyalkyl dithiocarbamates and use as ore flotation reagents" 1985, US; U.S. Pat. No. 4,554,108A; and Frank, A. W. "*Stability of Salts of N-Carboxy, N-Thiocarboxy and N-Dithiocarboxyglycine*" Phosphorus, Sulfur and Silicon 1990, 54, 109. Korner, H. "*Über einige Derivate der Dithiocarbamino-essigsäure*" Berichte der deutschen chemischen Gesellschaft 1908, 41, 1901, or Valentine, W. M.; Amarnath, V.; Graham, D. G.; Anthony, D. C. "*Covalent cross-linking of proteins by carbon disulfide*" Chem. Res. Toxicol. 1992, 5, 254.

Preparation A for the dithiocarbamate potassium salts.

In a 1L round bottom flask the amino acid (1mol) is dissolved in water 200 mL and KOH (112 g; 2 mol) is added. Once the exotherm settles, CS2 (152 g; 2 mol) is added slowly. The mixture slowly turns to yellow (~10 min). The reaction mixture is stirred at room temperature for 24 hours. The solvents and excess CS2 are then removed under vacuum. The reaction product is either kept as is in solution in water or acetonitrile (100 mL) is added to form an azeotrope to facilitate the removal of water. In the latter case the resulting solid is kept under vacuum for 10 days and chunks are broken in cold to afford a very hygroscopic yellow to pink powder that is kept under nitrogen.

Preparation B for the dithiocarbamate ammonium salts.

To a 125 mL round bottom flask the corresponding amine starting material (35 mmol) with 30 mL of diethyl ether are added and stirred to form a homogenous solution. Triethylamine (12 g; 53 mmol) is then slowly added to the mixture at room temperature and once the addition is complete, $CS_2$ (4 g; 53 mmol) is added drop wise. The flask is sealed and the solution is stirred overnight. The excess CS2, diethyl ether, and triethylamine are removed under vacuum to afford a solid (yield 95-99%). The product is finally dissolved in 10 mL of deionized water to be handled and tested as a 50% wt solution.

Preparation C for the diethanolamine dithiocarbamate potassium salts.

In a 250 mL round bottom flask add KOH (5.6 g) as a 60 wt % in water/EtOH (20/80). Stir the solution vigorously and slowly add water dropwise until all of the KOH pellets have dissolved then add diethanolamine (21 g) slowly. Once the exotherm has settled at room temperature, add carbon disulfide (7.6 g) to the round bottom flask slowly and close with flask with a glass stopper. Let the solution stir vigorously for 2 hours, then add ethanol (20 mL) to precipitate out the product. Filter the solid and wash it with ethanol. Dry the isolated product in a rotary evaporator to remove any excess ethanol.

Dithiocarbamate amide derivatives (e.g., the dithiocarbamate of 3-(methylamino)propionamide) are not exemplified due to the fact that the starting material is expensive and only available in small quantities. However, such compounds could be made in the same fashion as above with only routine modification to the processes as outlined.

Characterization of the various compounds synthesized is provided in Table 2 below.

These pH conditions must be determined for each component before studying the blending.

A1. Stability of AERO® 7260 HFP at Different pH.

To a stifling sample of AERO® 7260 HFP (Lot # AQ30130UJ; initial pH=7.4) the required amount of an aqueous NaOH 10 wt. % is added dropwise to adjust pH to 8, 10 or 12. Water is added so that the polymer concentration is the same for all the different samples. Samples are sealed in a glass jar and aged on the bench at room temperature and at 45° C.

The aging of AERO® 7260 HFP at different pH is monitored by NMR. The findings are summarized below in Table 3.

TABLE 2

Characterization of dithiocarbamate compounds.

| Name | Prep. | Yield %[a] | $^1$H-NMR[b] | $^{13}$C-NMR[b] | LCMS (ESI) m/z |
|---|---|---|---|---|---|
| CDTC | A | 99 | 4.18 | 211.7; 176.8; 51.6 | 298.932 [2M + H]$^-$ |
| SDTC | A | 99 | 4.81, 3.66 | 209.23, 75.96, 60.65, 44.44 | 279.8673 [M + K] |
| TDTC | A | 89 | 4.08, 3.41 | 211.85, 50.39, 43.48 | 199.9510 [M − H]$^-$ |
| IDTC | A | 100 | 3.23 | 211.58, 176.54, 59.52 | 207.9782 [M − H]$^-$ |
| BDTC | A | 97 | 3.80, 2.60 | 210.58, 180.61, 45.42, 36.25 | 163.9868 [M − H]$^-$ |
| ADTC | A | 88 | 3.61, 2.30, 1.94 | 210.29, 182.74, 48.21, 35.33, 25.17 | 178.0031 [M − H]$^-$ |
| GDTC | A | 77 | 2.32, 2.14, 1.98 | 211.42, 182.32, 179.03, 63.32, 34.35, 28.62 | 221.9911 [M − H]$^-$ |
| EDTC | B | 100 | 3.54, 3.47, 2.91, 1.06 | 212.11, 59.70, 49.71, 46.47, 8.92 | 135.9890 [M]− |
| DDTC | B | 98 | 4.31, 3.92, 3.25, 1.33 | 214.61, 61.37, 58.27, 47.65, 9.71 | 180.0154 [M]− |
| PDTC | B | 91 | 3.46 (2H), 3.03, 1.64, 1.10 | 210.69, 59.30, 46.71, 44.84, 30.75, 8.58 | 150.0049 [M]− |
| KDTC | C | 88 | 4.21, 3.88 | 211.27, 59.17, 56.84 | 180.0154 [M]− |

[a]Yields are reported as amine starting material conversion by NMR.

[b]NMR 400 MHz Avance II in D$_2$O

Example 2—Definition of the Parameters for Blending AERO® 7260 HFP with CDTC

Depressants are in general water soluble molecules since they are designed to modify the non-value mineral surface to be hydrophilic. This is the case of CDTC and AERO® 7260 HFP that are both water soluble. Blending the two together in water although seemingly trivial does not provide a physically and chemically stable product easily, a set of specific conditions must be determined. For the miscibility of AERO® 7260 HFP (A) with the small molecule CDTC (B) in aqueous solution three parameters are considered: pH; ratio of A to B and total activity in weight %. All three parameters are clearly defined and ranges are outlined in the following sections.

A. Definition of pH Ranges, Stability of Components pH of aqueous blends is an important parameter influencing solubility and miscibility but it is also very important in terms of chemical stability. Indeed, all the compounds here can degrade or decompose under certain pH conditions.

TABLE 3 mol % hydrolysis of acrylamide moiety over time at different temperature and pH

| | | entry | | | | | |
|---|---|---|---|---|---|---|---|
| | | 1 | 2 | 3 | 4 | 5 | 6 |
| | | Temp. | | | | | |
| | | 23° C. | 23° C. | 23° C. | 23° C. | 45° C. | 45° C. |
| | | pH | | | | | |
| | | pH 12 | pH 10 | pH 8 | pH 7.4 | pH 7.4 | pH 12 |
| Time (day) | 0 | 1.83% | 0.00% | 0.00% | 0.00% | 0.44% | 3.76% |
| | 6 | — | — | — | — | 0.76% | 9.94% |
| | 8 | — | — | — | — | 0.32% | 10.95% |
| | 16 | 4.84% | 2.35% | 0.00% | 0.00% | — | — |
| | 29 | — | — | — | — | 0.92% | 19.13% |
| | 35 | 9.96% | 4.41% | 0.00% | 0.00% | — | — |
| | 60 | 11.85% | 6.69% | 0.81% | 0.55% | — | — |
| | 82 | 13.00% | 7.29% | 0.15% | 0.48% | — | — |

TABLE 3-continued mol % hydrolysis of acrylamide moiety over time at different temperature and pH

| | entry | | | | | |
|---|---|---|---|---|---|---|
| | 1 | 2 | 3 | 4 | 5 | 6 |
| | | | Temp. | | | |
| | 23° C. | 23° C. | 23° C. | 23° C. | 45° C. | 45° C. |
| | | | pH | | | |
| | pH 12 | pH 10 | pH 8 | pH 7.4 | pH 7.4 | pH 12 |
| 109 | 15.12% | 9.79% | 0.81% | 0.75% | — | — |
| 214 | 20.32% | 13.78% | 0.55% | 0.4% | — | — |

It is clear that pH 10 and above causes acrylamide (AMD) degradation although relatively slowly, 13.78 mol % of AMD are hydrolyzed in 214 days. AERO® 7260 HFP depressing performance is slightly affected by the amount of AMD mol % hydrolysis. Therefore, it is necessary to find blending conditions where no hydrolysis could happen.

AERO® 7260 HFP Stability Range pH≤9.

A2. Stability of CDTC at Different pH.

In a 4 dram vial equipped with a stir bar, CDTC (1 g, 4.40 mmol) is added to 3 mL water and 1 mL $D_2O$. Then, the pH is adjusted with 25 wt. % $H_2SO_4$ while stirring and internal standards, dimethylformamide (0.1 g, 1.37 mmol) and acetonitrile (0.09 g, 2.19 mmol), are added. 100 μL of the solution is transferred to a 5 mm NMR tube. The sample is analyzed by 1H and 13C NMR and potential decomposition of CDTC is recorded over up to 50 days. A sample similarly prepared in a NMR tube is incubated at 45° C. for 21 days in an oven and CDTC decomposition is also recorded by NMR.

Dithiocarbamates can decompose back to the starting amine in aqueous solution when pH is below a certain limit that is difficult to predict. NMR monitoring experiments at pH from 0 to 10 over time at room temperature and 45° C. are done to gather experimental data on CDTC aqueous stability. It is determined that CDTC is stable over at least 50 days at room temperature and at least 20 days at 45° C. between 7<pH<10. CDTC is also stable at pH 5 and 6 at room temperature over 3 days of monitoring (no more data points are taken after that time). Significant decomposition is observed within a few hours when pH is lower than 5 and complete decomposition is attained at pH 0 within the time of the experiment. Complete results are reported in Table 4 and Table 5 below.

TABLE 4

Stability of CDTC under neutral/basic conditions at room temperature ("RT") (i.e.. 20° C.-27° C.).

| Sample ID | pH | T (° C.) | time (d) | 1H *CDTC % | 13C *CDTC % | 1H *Gly % | 13C *CDTC % |
|---|---|---|---|---|---|---|---|
| A2-1 | 7 | RT | 0 | 100.0 | 100.0 | 100.0 | 100.0 |
| A2-2 | 7 | RT | 21 | 86.0 | 91.4 | 90.9 | 97.3 |
| A2-3 | 7 | RT | 51 | 83.9 | 93.2 | 91.3 | 94.2 |
| A2-4 | 8 | RT | 0 | 100.0 | 100.0 | 100.0 | 100.0 |
| A2-5 | 8 | RT | 21 | 87.9 | 91.9 | 92.2 | 98.3 |
| A2-6 | 8 | RT | 51 | 84.2 | 92.7 | 91.7 | 121.0 |
| A2-7 | 9 | RT | 0 | 100.0 | 100.0 | 100.0 | 100.0 |
| A2-8 | 9 | RT | 21 | 90.9 | 92.2 | 92.7 | 99.3 |
| A2-9 | 9 | RT | 51 | 89.4 | 94.9 | 93.1 | 97.2 |
| A2-10 | 10 | RT | 0 | 100.0 | 100.0 | 100.0 | 100.0 |
| A2-11 | 10 | RT | 21 | 92.2 | 97.4 | 92.7 | 99.1 |
| A2-12 | 10 | RT | 51 | 88.8 | 95.3 | 91.8 | 94.7 |

*remaining % of CDTC or glycine are calculated based on peak integral ratios of CDTC(Gly) to DMF. Day 0 is set to 100%.

TABLE 5

Stability of CDTC under neutral/basic conditions at 45° C.

| Sample ID | pH | T (° C.) | time (d) | 1H *CDTC % | 13C *CDTC % | 1H *Gly % | 13C *CDTC % |
|---|---|---|---|---|---|---|---|
| A2-13 | 7 | RT | 0 | 100.0 | 100.0 | 100.0 | 100.0 |
| A2-14 | 7 | 45 | 21 | 89.1 | 95.3 | 97.8 | 98.0 |
| A2-15 | 8 | RT | 0 | 100.0 | 100.0 | 100.0 | 100.0 |
| A2-16 | 8 | 45 | 21 | 102.6 | 100.2 | 99.5 | 99.3 |
| A2-17 | 9 | RT | 0 | 100.0 | 100.0 | 100.0 | 100.0 |
| A2-18 | 9 | 45 | 29 | 105.0 | 109.4 | 99.6 | 99.6 |
| A2-19 | 10 | RT | 0 | 100.0 | 100.0 | 100.0 | 100.0 |
| A2-20 | 10 | 45 | 29 | 99.1 | 116.3 | 103.7 | 99.6 |

*remaining % of CDTC or glycine are calculated based on peak integral ratios of CDTC(Gly) to DMF. Day 0 is set to 100%.

B. Ratios of Small Molecule and AERO® 7260 HFP.

Ranges of ratios are dictated by the Cu—Mo separation application needs. CDTC is a solid and AERO® 7260 HFP is a water solution with an activity commonly estimated at 30 wt % (mass fraction). This can lead to confusion when talking about ratios and total activity. Herein, the ratio, expressed in wt. %, is defined as the amount of solid small molecule CDTC (pure) in a mixture of this solid and an AERO® 7260 HFP dissolution. For example, in a 100 g mixture a ratio of 30 wt. % would be 30 g of the small molecule CDTC as a solid and the remainder 70 g are composed by the AERO® 7260 HFP solution. CDTC (Mw=227) ratios to be blended 30, 50 or 70 wt. %.

C. Total Activity, Concentration of Solids in Solution.

The activity of the mixture is defined as the total actual amount of solids in wt. %. The amount of AERO® 7260 HFP is accounted as solid, the water it carried counted for the total water in the mixture. A low limit of 15 wt. % is set because lower activities are believed uneconomical. 25 or 35 wt. % are made. The study started by making the 15 wt. % total activity blends. The 25, 35 or higher wt. % blends are made only if the 15 wt. % survived after 2 days.

Example 3—Blending Results of AERO® 7260 HFP with CDTC

The parameters defined above can be summarized as follows: pH range of stability of both depressants: 7 to 10; total activity defined as the total actual amount of solids in wt. %: 15 wt. %; 25 wt. %; 35 wt. %; or 40 wt. %; ratio of second depressant (CDTC): 30, 50 or 70 wt. %.

Based on the above parameters, a number of examples of combinations of ratios, activity and pH of AERO® 7260 HFP and CDTC blends are tested to find the most physically and chemically stable composition that performs in flotation. General preparation of blends of AERO® 7260 HFP and CDTC is outlined below.

In a vial 9 to 30 g, typically 15 g, of a specific blend (see Table 6 for specific quantities of material) is prepared and analyzed as follows. CDTC (1.3-8.1 g) is added to water (6.9-13.8 g) and the mixture is vortexed for a minute. If CDTC is not completely dissolved at room temperature, the blend is put in a 45° C. oven. After all the solids are dissolved, the pH of the blend is adjusted with either 25 wt. % NaOH (for pH 10 blends) or 25 wt. % H2SO4 (for blends with a pH<10) at room temperature (22° C.). Then AERO® 7260 HFP (0.9-8 g) is added and the pH is adjusted again if necessary. The samples are aged at room temperature and continuously monitored for 6 months or until the material precipitated out. Physical stability is visually assessed and chemical stability is monitored by 1H and 13C NMR analyses since time zero. NMR experiments are acquired on 50 µL sample of the blend with 30 µL $D_2O$ in 5 mm NMR tubes. In a similar fashion, selected samples of 30 g are prepared and transferred to the vapor pressure monitoring instrument to incubate them at a set temperature (usually 45° C.). The pressure variation of each sample is continuously recorded for period of times ranging from 15 to 45 days. The samples are analyzed by 1H and 13C NMR at time zero and after ageing. A summary of blends is provided in Table 6, below.

B. Chemical Stability

All blend samples are monitored by NMR at room temperature over months to assess their chemical integrity and selected samples are monitored at 45° C. for several weeks.

At room temperature no substantial degradation of either CDTC or AERO® 7260 HFP is observed over the course of months in any blend across the whole range of activities, ratios of components and pH except in one instance. At pH 10 and high concentration in CDTC (Sample 3-7) chemical degradation is recorded after 6 months at room temperature.

Selected blends (Samples 3-7, 3-9, 3-17 and 3-18) are incubated at 45° C. in the vapor pressure monitoring instrument over 28 days and negligible pressure increase is observed. Samples at pH 8 (Samples 3-17 and 3-18) did not show signs of chemical degradation. However, samples at pH 10 showed chemical degradation by NMR (Samples 3-7 and 3-9).

Preferred blends include Samples 3-17 and 3-18—pH: 8; Total activity: 35 wt. %; Ratio: 50 to 70 wt. % CDTC.

TABLE 6

Examples of AERO ® 7260 HFP/CDTC blends at different activity, ratios and pH and their physical and chemical stability.

| | Conditions | | Mass | | | | Stability at room temp. | | | Chemical stability |
|---|---|---|---|---|---|---|---|---|---|---|
| | | | | AERO | | $H_2SO_4$ | | | | |
| Sample ID | pH | Activity (Wt. %) | Ratio (Wt. %) | Total (g) | 7260 (g) | CDTC (g) | NaOH (g) | Time (days) | Physical | Chemical | at 45° C. for 28 days |
| 3-1 | 10 | 15 | 70 | 15 | 0.86 | 1.99 | 0.14 | 185 | yes | yes | — |
| 3-2 | 10 | 15 | 50 | 15 | 1.73 | 1.73 | 0.16 | 185 | yes | yes | — |
| 3-3 | 10 | 15 | 30 | 15 | 3.09 | 1.32 | 0.12 | 185 | no | — | — |
| 3-4 | 10 | 25 | 70 | 15 | 1.43 | 3.32 | 0.11 | 181 | yes | yes | — |
| 3-5 | 10 | 25 | 50 | 15 | 2.89 | 2.88 | 0.17 | 181 | yes | yes | — |
| 3-6 | 10 | 25 | 30 | 15 | 5.14 | 2.21 | 0.21 | 181 | no | — | — |
| 3-7 | 10 | 35 | 70 | 20 | 2.66 | 6.2 | 0.12 | 161 | yes | no | no |
| 3-8 | 10 | 35 | 50 | 30 | 8.07 | 8.08 | 0.27 | 140 | yes | yes | — |
| 3-9 | 10 | 35 | 30 | 15 | 7.2 | 3.09 | 0.03 | 167 | no | — | no |
| 3-10 | 10 | 40 | 70 | 15 | 2.28 | 5.32 | 0.08 | 160 | yes | yes | — |
| 3-11 | 10 | 40 | 50 | 15 | 4.62 | 4.61 | 0.16 | 160 | yes | yes | — |
| 3-12 | 10 | 40 | 30 | 15 | 8.24 | 3.53 | 0.19 | 160 | no | — | — |
| 3-13 | 7 | 35 | 70 | 15 | 1.99 | 4.65 | 0.48 | 74 | no | — | — |
| 3-14 | 7 | 35 | 30 | 15 | 7.21 | 3.09 | 0.3 | 74 | no | — | — |
| 3-15 | 7 | 40 | 70 | 15 | 2.28 | 5.32 | 0.41 | 153 | no | — | — |
| 3-16 | 7 | 40 | 30 | 15 | 8.24 | 3.53 | 0.4 | 73 | no | — | — |
| 3-17 | 8 | 35 | 70 | 15 | 1.99 | 4.65 | 0.17 | 41 | yes | yes | yes |
| 3-18 | 8 | 35 | 50 | 9 | 2.43 | 2.43 | 0.14 | 12 | yes | yes | yes |
| 3-19 | 8 | 35 | 30 | 15 | 7.21 | 3.09 | 0.17 | 41 | no | — | — |
| 3-20 | 8 | 40 | 70 | 9 | 1.37 | 3.19 | 0.22 | 34 | no | — | — | a. Physical Stability pH 10 blends offer the largest window of ratios and highest activity (e.g., Samples 3-1-3-5; 3-7; 3-8; 3-10; and 3-11). However, based on the chemical stability data collected it seems reasonable to lower the pH closer to neutral.

Blending at a 35 wt. % activity and pH 7 required the addition of acid in concentrations that led to the precipitation of salts (Samples 3-13-3-16). pH 8 is ideal to keep everything in solution and allowed 35 wt. % activity. However, this could only be attained with ratios of AERO® 7260 HFP to CDTC of 30/70 and 50/50, meaning at low polymer content (Samples 3-17 and 3-18). Low polymer ratios are observed to perform the best.

Example 4—Blending Results of AERO® 7260 HFP with Other Dithiocarbamate Compounds Using the previous parameters as in Example 3 the other dithiocarbamate derivatives were blended with AERO® 7260 HFP successfully. The different formulations were physically and chemically stable after 12 days at room temperature as shown in Table 7. Physical stability means that the blend was miscible and no polymer or other solid precipitation was observed. Chemical stability means that the blends did not show any signs of degradation comparing to the starting materials by the typical chemical analyses (NMR, pH).

TABLE 7

Blends of AERO ® 7260 HFP and various dithiocarbamate derivatives

| | | Conditions | | | Mass | | | Stability at room temp. | | |
|---|---|---|---|---|---|---|---|---|---|---|
| | | | DTC | AERO | | | | | | |
| Smpl # | DTC Deriv. | pH | Activity (Wt. %) | ratio (Wt. %) | Total (g) | 7260 (g) | DTC (g) | H$_2$SO$_4$ (g) | Time (days) | Physical | Chemical |
| 4-1 | BDTC | 8.92 | 47.73 | 61 | 5.1 | 0.8 | 3.05 | 0.1 | 12 | Yes | Yes |
| 4-2 | ADTC | 8.74 | 55.52 | 61 | 5.1 | 0.8 | 3.05 | 0.1 | 12 | Yes | Yes |
| 4-3 | GDTC | 8.09 | 53.34 | 61 | 5.11 | 0.8 | 3.05 | 0.11 | 12 | Yes | Yes |
| 4-4 | IDTC | 7.64 | 49.61 | 61 | 5.03 | 0.8 | 3.05 | 0.03 | 12 | Yes | Yes |
| 4-5 | TDTC | 8.77 | 65.33 | 61 | 5.08 | 0.8 | 3.05 | 0.08 | 12 | Yes | Yes |
| 4-6 | SDTC | 8.27 | 55.85 | 61 | 5.05 | 0.8 | 3.05 | 0.05 | 12 | Yes | Yes |
| 4-7 | BDTC | 8.92 | 47.73 | 43.21 | 10.03 | 2.35 | 6.39 | 0.14 | 13 | Yes | Yes |
| 4-8 | ADTC | 7.98 | 55.52 | 42.28 | 9.52 | 2.35 | 5.49 | 0.53 | 13 | Yes | Yes |
| 4-9 | GDTC | 8.32 | 53.34 | 42.53 | 9.54 | 2.35 | 5.71 | 0.33 | 13 | Yes | Yes |
| 4-10 | DDTC | 9.01 | 35.69 | 44.75 | 12.13 | 2.35 | 8.54 | 0.09 | 13 | Yes | Yes |
| 4-11 | EDTC | 9.01 | 47.31 | 43.27 | 10.23 | 2.35 | 6.44 | 0.29 | 13 | Yes | Yes |
| 4-12 | PDTC | 8.25 | 43.8 | 43.7 | 10.46 | 2.35 | 6.96 | 0 | 13 | Yes | Yes |

Example 5—Blend Performance in Cu—Mo Separation

The two depressants (AERO® 7260 HFP and CDTC) are blended at appropriate ratios to produce a composition that is chemically and physically stable and safer to use under operating conditions common in Cu—Mo operations. The composition provides sufficient depression of copper sulfides and pyrite at appropriate ratios and dosages without negative effects on molybdenite flotation. All percentages are by weight and all dosages are for 30 wt. % solutions unless otherwise specified.

A. Sample Nos. 5A-1-5A-12

In these examples, a Cu—Mo bulk concentrate (A) containing 28% Cu and 1.8% Mo is used. The objective is to selectively depress copper sulfides and float molybdenite. The Cu occurrences in this bulk concentrate are predominantly chalcopyrite. The bulk concentrate also contains a small amount of pyrite and non-sulfide gangue minerals (mostly aluminum silicates). Molybdenite is the only molybdenum mineral in the bulk concentrate.

The pulp is a concentrate from the bulk circuit and therefore does not need to be ground again for the first stage of Cu—Mo separation (rougher stage). The pulp is split into 800 ml flotation charges and stored in a freezer at −15° C. to minimize aging and oxidation. Before being used for rougher flotation tests, 800 ml of the frozen slurry is thawed for 30 minutes using warm water and then added to a 1.7 L flotation cell. The volume in the flotation cell is brought to approximately 2.5-3 cm below the cell lip by adding lab tap water to achieve a solids content in the range of 25-35 wt. %. The slurry is agitated at 900 rpm and the pH is then adjusted to approximately 10.5 with a 50 wt. % solution of NaOH. The target pH can also be achieved using lime. Diesel fuel at 10 g per ton of solids is then added as a molybdenite collector while a frother of the polyglycol or alcohol or alcohol/polyglycol blend is added at 10 g per ton of solids as required.

The slurry is then conditioned with depressant systems shown in Table 8 for 10 minutes. The conditioning time varies with the bulk concentrate mineralogy and can be as high as 30 minutes. The depressants can be co-dosed separately into the flotation cell or they can be made into a formulation and added as a blend. In Samples 5A-8-5A-12, CDTC and AERO® 7260 HFP are added separately into the flotation cell. The depressants are preferably added to the flotation cell in solution form in order to ensure dispersibility in the pulp, but CDTC can be added in solid form as well. Flotation is then conducted by passing air through the slurry and collecting timed concentrates over a period of 8 minutes. Nitrogen may be used as the flotation gas in place of air. The concentrates and tailings are filtered, dried in an oven at 80° C., weighed and assayed for Cu and Mo.

A comparison of the standard depressants (NaSH and NaSH+AERO® 7260 HFP) and depressant combinations of this invention is shown in Table 8 below. Since the objective in these examples is to depress copper sulfides and float molybdenite, satisfactory performance is indicated by high depressant activity (low Cu recovery) and high selectivity (low Cu recovery and high Mo recovery). The success criterion is dependent on the NaSH and NaSH+AERO® 7260 HFP standard tests. For the Cu—Mo bulk concentrates evaluated in these examples, acceptable performance of a depressant requires Cu recoveries less than 20% and Mo recoveries greater than 90%. Minor excursions from these set points, say of ±1% are acceptable and are typical in industry given the variability in Cu—Mo separation tests.

TABLE 8

| Sample No. | Depressant | Dosage, kg/t, 30% solution | CDTC plus 7260 Dosage, kg/t | Ratio of 7260 to CDTC | Copper Recovery, % | Mo Recovery, % |
|---|---|---|---|---|---|---|
| 5A-1 | None | — | — | — | 99.5 | 99.3 |
| 5A-2 C | NaSH | 25.5 | — | — | 15.9 | 97.7 |
| 5A-3 C | NaSH plus 7260 | 2.3 0.84 | — | — | 10.6 | 96.5 |
| 5A-4 | CDTC | 7.1 | — | 0:100 | 34.6 | 99.9 |
| 5A-5 | CDTC | 20.2 | — | 0:100 | 18.9 | 92.9 |

TABLE 8-continued

| Sample No. | Depressant | Dosage, kg/t, 30% solution | CDTC plus 7260 Dosage, kg/t | Ratio of 7260 to CDTC | Copper Recovery, % | Mo Recovery, % |
|---|---|---|---|---|---|---|
| 5A-6 | 7260 | 0.91 | — | 100:0 | 83.2 | 93.5 |
| 5A-7 | 7260 | 2.77 | | 100:0 | 7.6 | 41.8 |
| 5A-8 | CDTC plus 7260 | 7.50 1.00 | 8.50 | 29:71 | 9.5 | 95.5 |
| 5A-9 | CDTC plus 7260 | 5.30 0.99 | 6.29 | 36:64 | 10.6 | 94.9 |
| 5A-10 | CDTC plus 7260 | 3.18 0.79 | 3.97 | 43:57 | 13.7 | 91.1 |
| 5A-11 | CDTC plus 7260 | 3.97 1.13 | 5.10 | 46:54 | 12.8 | 87.3 |
| 5A-12 | CDTC plus 7260 | 2.50 0.84 | 3.34 | 50:50 | 13.5 | 90.4 |

Sample 5A-1 demonstrates that the copper sulfides and molybdenite readily float in the absence of a depressant which indicates that the Cu—Mo bulk concentrates are suitable for evaluation of depressants. Samples 5A-2 C and 5A-3 C are prior art sulfide depressants that are currently used in industry and provided for comparative purposes. With NaSH only, a high dosage (25.5 kg/t) is required to obtain satisfactory performance (15.9% Cu recovery and 97.7% Mo recovery). The high dosage of NaSH required in Sample 5A-2 C can be explained by its oxidation during the process of Cu—Mo separation. This oxidation necessitates addition of large amounts of NaSH to maintain pulp potentials more negative than approximately −500 mV during the course of the Cu—Mo separation process. The very high dosage of NaSH can be reduced with the use of a small dosage of AERO® 7260 HFP (0.84 kg/t). Only 2.3 kg/t of NaSH is required when the polymer is used.

Samples 5A-4 and 5A-5 are conducted using a prior art sulfide depressant (CDTC), a component of the inventive blend. At a low dosage of 7.1 kg/t, CDTC does not provide adequate Cu depression (Cu recovery is 34.6%) while Mo recovery of 99.9% is satisfactory. Being a small molecule, CDTC exhibits satisfactory depressant activity at a high dosage as demonstrated in Sample 5A-5. The Cu recovery (18.9%) using 20.2 kg/t of CDTC is slightly lower than that obtained with the standard depressants, thus more effective Cu depression may be obtained at a higher dosage comparable to that required with NaSH. Thus, although CDTC alleviates the safety, health and environmental hazards associated with the use of NaSH, the very high dosages required for adequate performance would not be cost-effective given the higher cost of making CDTC relative to the NaSH price.

The depressant system of this invention (CDTC+AERO® 7260 HFP) provides a way to reduce the very high dosages of CDTC as demonstrated in Samples 5A-8-5A-12 with the use of CDTC and the polymer (AERO® 7260 HFP). It must be noted that the polymer of the first depressant (e.g., AERO® 7260 HFP) by itself, at any dosage, does not provide satisfactory performance. This is demonstrated in Samples 5A-6 and 5A-7 where Cu depression is unsatisfactory at a low dosage of 0.91 kg/t (Cu recovery is 83.4%) while both Cu and Mo are depressed at a higher dosage of 2.77 kg/t. It must also be noted that NaSH is not required for use with the depressant compositions according to the invention described and claimed herein. This is significant since the safety, health and environmental hazards associated with the use of even small amounts of NaSH (such as in the case of the standard depressant system NaSH+ AERO® 7260 HFP) are eliminated.

Due to the poor selectivity of AERO® 7260 HFP at high dosage, poor Cu depression at low dosage, and poor Cu depression at low dosage, combined use of AERO® 7260 with CDTC is not straightforward. In particular, finding the appropriate ratio of AERO® 7260 HFP to CDTC and effective dosages is an involved process. Accordingly, the superior results obtained in the studies exemplified herewith could not simply have been expected by one of ordinary skill in the art at the time of invention.

Very good selectivity is achieved when the ratio of CDTC to AERO® 7260 HFP ranges from 29:71 to 36:64 at overall blend dosages of 8.5 kg/t and 6.3 kg/t respectively (Samples 5A-8 and 5A-9). At these ratios and blend dosages, the dosage of AERO® 7260 HFP is approximately 1 kg/t while that of CDTC ranges from 5.3 kg/t to 7.1 kg/t. One way to reduce the overall blend dosages is by increasing the amount of amount of AERO® 7260 HFP in the blend to exploit its superior depressant activity relative to CDTC. This is demonstrated in Sample 5A-10 (AERO® 7260 HFP:CDTC ratio of 43:57) where the total blend is decreased to 3.97 kg/t and the depressant activity (Cu recovery of 13.7%) and selectivity (Mo recovery of 91.1%) is maintained.

An important aspect of the Cu—Mo separation process is the dosage range under which selectivity is maintained. It is often the practice in industry to increase depressant dosage in order to manage changes in ore mineralogy or changes in process conditions such as water chemistry, type and amount of collector used in the bulk circuit preceding the Cu—Mo separation process. In the depressant systems of this invention, the ratio of AERO® 7260 HFP to CDTC is important since it determines the dosage range in which the depressant system can be used without compromising selectivity. In Sample 5A-8, the ratio of AERO® 7260 HFP to CDTC (29:71) is such that selectivity can be maintained even at a very high dosage. In the example, a dosage of 8.5 kg/t provides excellent selectivity. However, in the case where more AERO® 7260 HFP is used such as in Sample 5A-11 (ratio of AERO® 7260 HFP:CDTC is 46:54), a much lower total dosage of 5.1 kg/t (3.97 kg/t of CDTC+1.13 kg/t of AERO® 7260 HFP) is not quite satisfactory as can be seen from the lower Mo recovery of 87.3%. At this ratio, a lower dosage has to be used clearly indicating that the operating dosage range for a AERO® 7260 HFP:CDTC ratio of 46:50 would not be as wide as that for the 29:71 ratio. In Sample 5A-12, it is indeed demonstrated that improved selectivity is obtained for the 50:50 ratio if a lower dosage of 3.34 kg/t (2.5 kg/t of CDTC+0.84 kg/t of AERO® 7260 HFP) is used.

The results in Table 8 indicate clearly that the use of a combination of AERO® 7260 HFP and CDTC is superior to that of either AERO® 7260 or CDTC when used alone from a metallurgical and dosage efficiency point of view. The results also indicate that use of AERO® 7260 HFP and CDTC to achieve satisfactory Cu—Mo separation requires careful choice of dosages and ratio of the two depressants.

B. Sample Nos. 5B-1-5B-12

Using the procedure set forth in Example 5A, the performance of blends of CDTC analogs described in Example 1 and AERO 7260 HFP is investigated using a bulk concentrate (B) similar in location to that used in Example 5A, but which is more difficult to depress. For this Cu—Mo bulk concentrate, acceptable performance of the CDTC analog/ AERO® 7260 HFP blends requires Cu recoveries less than 30% and Mo recoveries greater than 90%. The results are provided in Table 9, below.

HFP effectively depress Cu sulfides effectively and provide the required selectivity. It should be noted that the dosages of the blends and ratios of each CDTC analog to AERO® 7260 HFP in Samples 5B4-5B-12 are unoptimized. Those skilled in the art will be able to obtain similar or better performance at low blend dosages by, for instance, changing the AERO® 7260 HFP:CDTC analog ratios using no more than routine experimentation.

C. Sample Nos. 5C-1-5C-14

The efficacy of CDTC+AERO® 7260 HFP and the effective dosage ranges are further demonstrated in Samples 5C-1-5C-14 using a different Cu—Mo bulk concentrate (C) containing 27.4% Cu and 0.6% Mo. The objective is once again to selectively depress Cu sulfides and float molybdenite. The same procedure as described in Example 5A is used, except that a lower pH of approximately 8.5 (achieved using a 25% sulfuric acid solution) is used. The mineralogy of concentrate (C) used in these examples is different from that used in Examples 5A (concentrate A) which demonstrates the robustness of CDTC+AERO® 7260 HFP. In addition to chalcopyrite, concentrate (C) contains secondary copper minerals chalcocite, bornite and tennantite. Concentrate (C) also contains a high amount of pyrite and non-sulfide gangue

TABLE 9

| Sample No. | Depressant | Dosage, kg/t, 30% solution | CDTC Analog plus 7260 Dosage, kg/t | Ratio of 7260 to CDTC Analog | Copper Recovery, % | Mo Recovery, % |
|---|---|---|---|---|---|---|
| 5B-1 | None | — | — | — | 99.9 | 98.7 |
| 5B-2 C | NaSH | 22.9 | — | — | 16.0 | 98.7 |
| 5B-3 C | NaSH plus 7260 | 5.84 1.14 | — | — | 13.3 | 96.2 |
| 5B-4 | SDTC plus 7260 | — | 6.09 | 37:63 | 18.3 | 97.0 |
| 5B-5 | TDTC plus 7260 | — | 7.86 | 34:66 | 17.8 | 94.8 |
| 5B-6 | BDTC plus 7260 | — | 6.21 | 41:59 | 24.8 | 97.7 |
| 5B-7 | ADTC plus 7260 | — | 6.82 | 37:63 | 23.9 | 96.2 |
| 5B-8 | GDTC plus 7260 | — | 9.57 | 38:62 | 22.8 | 95.8 |
| 5B-9 | DDTC plus 7260 | — | 8.10 | 40:60 | 17.4 | 95.9 |
| 5B-10 | EDTC plus 7260 | — | 9.28 | 40:60 | 13.8 | 94.2 |
| 5B-11 | PDTC plus 7260 | — | 7.12 | 43:57 | 29.6 | 94.8 |
| 5B-12 | IDTC plus 7260 | — | 7.60 | 40:60 | 30.5 | 97.4 |

Sample 5B-1 demonstrates that the copper sulfides and molybdenite readily float in the absence of a depressant which indicates that the Cu—Mo bulk concentrate (B) is suitable for evaluation of the CDTC analog/7260 blends. Samples 5B-2 C and 5B-3 C are prior art sulfide depressants that are currently used in industry and are provided for comparative purposes. With NaSH only, a high dosage (22.9 kg/t) is required to obtain satisfactory performance (16.0% Cu recovery and 98.7% Mo recovery). The very high dosage of NaSH can be reduced with the use of a small dosage of AERO® 7260 HFP (1.14 kg/t) without detriment to Cu—Mo separation. Only 5.84 kg/t of NaSH is required when the polymer is used (Sample 5B-3 C).

In Samples 5B-4-5B-12, results of the depressant activity and selectivity of blends of CDTC analogs of Example 1 and AERO® 7260 HFP are presented. It is evident from the results that blends of CDTC analogs with AERO® 7260 minerals relative to concentrate A. The results are given in Table 10. Due to the differences in mineralogy of concentrates A and (C), different success criteria (<25% Cu recovery, >90% Mo recovery) is used to evaluate the efficacy of the depressants.

Once again, Sample 5C-1 demonstrates the suitability of the Cu—Mo bulk concentrate for testing since almost all Cu sulfides and molybdenite can be floated in the absence of a depressant. Nokes, instead of NaSH, is used in concentrate (C) and is, therefore, used as the standard depressant in Sample 5C-2 C. The depressant in Sample 5C-3 C is a prior art depressant and has been used in industry and is, therefore, provided as a standard depressant for comparative purposes. The smaller amount of Nokes required in Sample 5C-3 C with AERO® 7260 HFP serves the same purpose as the small amount NaSH used in Sample 5A-3 C. Details are described in U.S. Pat. No. 4,866,150, for example.

TABLE 10

| Sample No. | Depressant | Dosage, kg/t, 30% solution | CDTC plus 7260 Dosage, kg/t | Ratio of 7260 to CDTC | Copper Recovery, % | Mo Recovery, % |
|---|---|---|---|---|---|---|
| 5C-1 | None | — | — | — | 99.1 | 99.7 |
| 5C-2 C | Nokes | 13.5 | — | — | 20.2 | 90.3 |
| 5C-3 C | Nokes plus | 4.6 | — | — | 20.7 | 92.9 |
| 5C-4 | CDTC | 19.3 | — | 0:100 | 20.7 | 97.2 |
| 5C-5 | 7260 | 1.54 | — | 100:0 | 72.6 | 85.5 |
| 5C-6 | 7260 | 2.04 | — | 100:0 | 17.5 | 75.4 |
| 5C-7 | CDTC | 4.11 | 4.64 | 30:70 | 18.3 | 92.5 |
| 5C-8 | CDTC | 6.44 | 7.27 | 30:70 | 21.4 | 94.0 |
| 5C-9 | CDTC | 10.2 | 11.5 | 30:70 | 18.3 | 92.0 |
| 5C-10 | CDTC | 12.9 | 14.5 | 30:70 | 17.7 | 92.2 |
| 5C-11 | CDTC | 5.48 | 6.65 | 40:60 | 15.9 | 90.1 |
| 5C-12 | CDTC | 4.54 | 5.90 | 50:50 | 24.4 | 92.7 |
| 5C-13 | CDTC | 7.29 | 9.48 | 50:50 | 19.5 | 88.0 |
| 5C-14 | CDTC | 10.9 | 14.1 | 50:50 | 10.1 | 62.6 |

The standard depressants all provide adequate Cu depression and acceptable Mo recovery. With CDTC only, performance comparable to that of the standard depressants is obtained at a very high dosage (Sample 5C-4). With AERO® 7260 HFP only, as observed with the concentrate A, satisfactory performance cannot be obtained since the polymer exhibits a low depressant activity when used at a low dosage (Sample 5C-5) and is non-selective at a higher dosage (Sample 5C-6). Samples 5C-7-5C-14, however, demonstrate that satisfactory Cu depression and Mo recovery can be obtained by using AERO® 7260 HFP in conjunction with CDTC and careful selection of the ratio of AERO® 7260 HFP to CDTC and the blend dosage. Samples 5C-7-5C-10 are conducted using the inventive blend of Sample 3-7 in Table 6 while Samples 5C-12 5C-14 are conducted using the inventive blend of Sample 3-8.

When the ratio of AERO® 7260 HFP to CDTC is 30:70, satisfactory performance is obtained in the dosage range of 4.64 kg/t to 14.5 kg/t. Such a wide dosage gives plant operators the desired flexibility to adjust depressant dosages while meeting product specifications. It can be seen that at the highest dosage (14.5 kg/t, Sample 5C-10), the dosage of AERO® 7260 HFP in the blend is 1.66 kg/t which is slightly higher than the dosage of AERO® 7260 HFP used in Sample 5C-5. However, despite the slightly higher AERO® 7260 HFP dosage in Sample 5C-10, better Mo recovery (92.2%) is obtained whereas Mo flotation is slowed down when AERO 7260 is used by itself in Sample 5C-5. It can be speculated that the presence of a large amount of CDTC in the blend of Sample 5C-10 helps to minimize the detrimental effect of a large dosage of AERO® 7260 HFP on Mo recovery.

In Sample 5C-11, a blend with a ratio of AERO® 7260 HFP to CDTC of 40:60 is used. At 6.65 kg/t, the amount of AERO® 7260 HFP in the blend is only 1.17 kg/t and this is sufficient to give satisfactory performance in conjunction with CDTC. When blends with a ratio of 50:50 are used in Samples 5C-12-5C-14, satisfactory performance can only be obtained at dosages less than approximately 9 kg/t. It is seen that as blend dosages as increased from 5.90 kg/t to 14.1 kg/t, the dosage of AERO® 7260 HFP also increases from 1.3 kg/t to 3.27 kg/t resulting in loss in selectivity especially at the highest dosage where Cu depression is excellent but Mo recovery of 62.6% is unacceptable.

The results in Table 10 demonstrate the efficacy of combinations of AERO® 7260 HFP and CDTC as selective depressants; they also clearly demonstrate that although satisfactory performance can be obtained using blends with ratios of AERO® 7260 HFP to CDTC ranging from 30:70 to 50:50, it is preferred to use the blend in which the ratio of AERO® 7260 HFP to CDTC is 30:70 since selectivity of Cu—Mo separation is achieved in a wide dosage range as desired in the plant.

D. Sample Nos. 5D-1-5D-5.

The efficacy of AERO® 7260 HFP+CDTC is yet again evaluated on a Cu—Mo bulk concentrate (D) that contains 24.4% Cu and a higher amount of Mo (5.4%). The predominant Cu sulfide mineral is chalcopyrite but there are minor amounts of tennantite. This concentrate is particularly hard to depress and requires a longer conditioning time (up to 20 minutes) than concentrates A and C which require only 10 minutes conditioning time. Also, the molybdenite in this concentrate floats slowly than that in concentrates A (Samples 5A) and concentrate C (Samples 5C). The same procedure described in Example 5A is used, except the longer conditioning time of approximately 20 minutes.

The results given in Table 11 indicate that the depressants of this invention are able to depress copper sulfide minerals in this difficult-to-process bulk concentrate, but that a small amount of NaSH is required to enhance the flotation of molybdenite when AERO® 7260 HFP+CDTC is used. The amount of NaSH required is a very small fraction of that required when NaSH is used by itself (Sample 5D-2 C) or when NaSH is used with AERO® 7260 HFP (Sample 5D-3 C). These examples indicate that the invention is able to depress a variety of Cu—Mo bulk concentrates and can be used with conventional inorganic depressant either to reduce overall depressant dosages or to enhance flotation of molybdenite that is oxidized or tarnished and therefore floats slowly.

TABLE 11

| Sample No. | Depressant | Dosage, kg/t, 30% solution | CDTC plus 7260 Dosage, kg/t | Ratio of 7260 to CDTC | Copper Recovery, % | Mo Recovery, % |
|---|---|---|---|---|---|---|
| 5D-1 | None | — | — | — | 98.3 | 93.6 |
| 5D-2 C | NaSH | 27.5 | — | — | 25.1 | 94.0 |
| 5D-3 C | NaSH plus 7260 | 8.3 1.17 | — | — | 24.0 | 91.7 |
| 5D-4 | CDTC plus 7260 | 4.06 0.51 | 6.56 | 30:70 | 22.5 | 84.4 |

TABLE 11-continued

| Sample No. | Depressant | Dosage, kg/t, 30% solution | CDTC plus 7260 Dosage, kg/t | Ratio of 7260 to CDTC | Copper Recovery, % | Mo Recovery, % |
|---|---|---|---|---|---|---|
| 5D-5 | CDTC plus 7260 plus NaSH | 4.06 0.51 1.06 | 5.63* | 30:70 | 21.7 | 93.0 |

*Includes NaSH for enhancing Mo flotation

E. Sample No. 5E-1-5E-3.

In this example, the same Cu—Mo bulk concentrate D used in Samples 5D-1 5D-5 above is used to demonstrate the effectiveness of CDTC+AERO® 7260 HFP as an iron sulfide depressant since it is desired in Cu—Mo operations to remove as much iron from the molybdenite concentrate as possible for environmental reasons. In this concentrate, iron occurs in chalcopyrite and pyrite, thus pyrite is considered as a gangue mineral and must be depressed in addition to chalcopyrite. Sample 5E-3 is conducted using the CDTC/AERO® 7260 HFP blend of Sample 3-7, Table 6. The results are given in Table 12. Samples 5E-1 (no depressants) and 5E-2 C (standard NaSH) are reproduced in Table 12 for comparison.

TABLE 12

| Sample No. | Depressant | Dosage, kg/t, 30% solution | CDTC plus 7260 Dosage, kg/t | Ratio of 7260 to CDTC | Iron Recovery, % |
|---|---|---|---|---|---|
| 5E-1 | None | — | — | — | 98.2 |
| 5E-2 C | NaSH | 27.5 | — | — | 26.6 |
| 5E-3 | CDTC plus 7260 plus NaSH | 4.63 0.58 1.21 | 6.42* | 30:70 | 21.9 |

*includes NaSH for enhancing Mo flotation

Without any depressants, almost all the iron floats into the concentrate giving a high iron recovery of 98.2%. When NaSH is used as the Cu sulfide depressant at 27.5 kg/t, iron recovery is reduced from 98.2% to 26.6% which is acceptable considering that this is a rougher flotation stage. Better iron depression (Fe recovery of 21.9% vs. 26.6% with NaSH) is obtained when a blend CDTC and AERO® 7260 HFP (plus a small amount of NaSH to enhance molybdenite flotation) is used as the depressant. The copper recovery is 23.4% while Mo recovery is 91.0% which are all satisfactory. The efficacy of the inventive depressant as a copper and iron sulfide depressant while maintaining high Mo recoveries is demonstrated clearly in this example. The better rejection of iron by CDTC+AERO® 7260 HFP relative to the standard NaSH is highly beneficial to operations which are faced with stringent Fe specifications from smelters.

F. Sample Nos. 5F-1-5F-5.

Sample 5F-4 in Table 13 demonstrates the efficacy of the first depressant (AERO® 7260 HFP) and a small amount of the second depressant (CDTC) as selective copper sulfide depressants when used in conjunction with sodium thioglycolate (NaTG), a small organic commercial depressant, and NaSH as surface modifying agents. Samples 5F-1 (no depressant), 5F-2 C and 5F-3 C (standard depressants) are provided for comparison purposes. A Cu—Mo bulk concentrate containing 24.7% Cu and 1.75% Mo is used.

TABLE 13

| Sample No. | Depressant | Dosage, kg/t, 30% solution | CDTC plus 7260 plus *NaTG plus NaSH Dosage, kg/t | CDTC plus NaTG* plus NaSH Dosage, kg/t | Cu Recovery, % | Mo Recovery, % |
|---|---|---|---|---|---|---|
| 5F-1 | None | — | — | — | 97.8 | 98.0 |
| 5F-2 C | NaSH | 23.2 | — | — | 11.8 | 94.2 |
| 5F-3 C | NaSH plus AERO® 7260 | 9.63 0.96 | — | — | 11.8 | 94.8 |
| 5F-4 | CDTC plus AERO® 7260 plus NaTG* plus NaSH | 1.70 0.77 0.27 0.82 | 3.56 | — | 12.9 | 91.1 |
| 5F-5 | CDTC plus NaTG* plus NaSH | 3.32 0.54 1.61 | — | 5.47 | 16.1 | 96.4 |

*Sodium thioglycolate

The performance achieved with CDTC+AERO® 7260 HFP+NaTG+NaSH is comparable to that of the standard depressants (NaSH or NaSH+AERO® 7260 HFP). The examples clearly demonstrate that the dosage of CDTC in the depressant system of this invention can be significantly reduced by using small amounts of commercially available surface modifying agents (NaTG and NaSH).

It must be noted that when CDTC, NaTG, and NaSH are used in the absence of AERO® 7260 HFP (Sample 5F-5), the dosage required to provide effective Cu depression and Mo recovery is 5.5 kg/ton. Thus, by using only 0.77 kg/t of AERO® 7260 HFP as shown in Sample 5F-4, the total depressant dosage is reduced significantly. This demonstrates that the polymeric efficiency of AERO® 7260 HFP is an essential feature of depressant systems capable of providing satisfactory metallurgical performance in Cu—Mo separations at reduced dosages.

Various patent and/or scientific literature references have been referred to throughout this application. The disclosures of these publications in their entireties are hereby incorporated by reference as if written herein. However, if a term in the present application contradicts or conflicts with a term in the incorporated reference, the term from the present application takes precedence over the conflicting term from the incorporated reference. In view of the above description and the examples, one of ordinary skill in the art will be able to practice the disclosure as claimed without undue experimentation.

Although the foregoing description has shown, described, and pointed out the fundamental novel features of certain embodiments of the present invention, it will be understood that various omissions, substitutions, and changes in the form of the detail of the invention as described may be made by those skilled in the art, without departing from the scope of the present teachings. Consequently, the scope of the present invention should not be limited to the foregoing description or discussion, but should be defined by the appended claims.

We claim:

1. A mineral flotation composition comprising an aqueous blend of a first depressant and a second depressant, wherein the first depressant is a polymer having a weight average molecular weight from 1,000 g/mol to 1,000,000 g/mol comprising:

i) X units of an acrylamide derivative according to Formula (I):

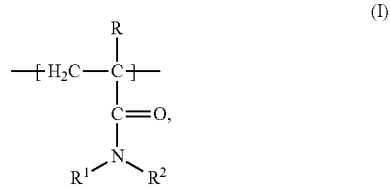

wherein each of R, $R^1$, and $R^2$ is independently chosen from H, $C_1$-$C_4$ alkyl, or $C_6$-$C_{12}$ aryl; and X is a residual mole percent fraction by weight based on the total mole percent by weight of Y and Z;

ii) Y units of a thiourea derivative according to Formula (II):

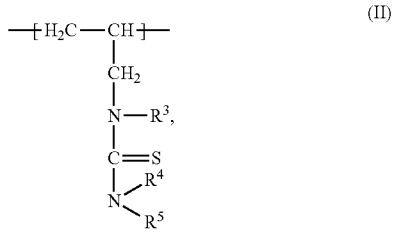

wherein $R^3$ is chosen from H, a $C_1$-$C_4$ alkyl, or $C_6$-$C_{12}$ aryl;

each of $R^4$ and $R^5$ is independently chosen from H, $C_1$-$C_4$ hydrocarbyl, or a $C_6$-$C_{12}$ aryl; and Y is a mole percent fraction from 1% to 50% by weight based on the total weight of X, Y, and Z;

wherein X units of Formula (I) to Y units of Formula (II) are present at a weight ratio in a range from 10:90 to 95:5; and iii) Z units of a polymerization residue of any monomer copolymerizable with the derivatives according to Formulas (I) and (II), wherein Z is a mole percent fraction from 0% to 50% by weight based on the total weight of X, Y, and Z; and wherein the second depressant is a dithiocarbamate compound according to Formula (III):

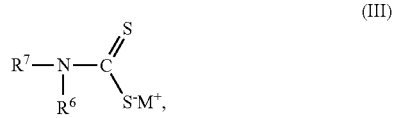

wherein $R^6$ is chosen from H, or a $C_1$-$C_4$ alkyl moiety having one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl;

$R^7$ is chosen from a $C_1$-$C_4$ alkyl moiety having one or more functional groups selected from OH, $SO_3^-M^+$, $COO^-M^+$, and $CONR^8R^9$, wherein each of $R^8$ and $R^9$ is independently chosen from H or $C_1$-$C_4$ alkyl; and each instance of M is independently chosen from a cation selected from the group consisting of alkali metal, metal, or $R^{10}_4N^+$, wherein each instance of $R^{10}$ is independently chosen from H or a $C_1$-$C_6$ alkyl, wherein the aqueous blend of the first depressant and second depressant is further characterized as having 4<pH≤14 at a temperature from −5° C. to 85° C.; and as being present at a weight ratio in a range from 20:80 to 80:20.

2. A mineral flotation composition according to claim 1, wherein the weight ratio of the first depressant to the second depressant is from 25:75 to 50:50.

3. A mineral flotation composition according to claim 1, wherein said blend of the first and second depressant is from 10 to 50 parts by weight, per 100 parts by weight of water, and having 4<pH≤14 at a temperature from 20° C. to 50° C.

4. A mineral flotation composition according to claim 1, wherein each of R, $R^1$, $R^2$, $R^3$, $R^4$, and $R^5$ is H.

5. A mineral flotation composition according to claim 1, wherein said first depressant has a weight average molecular weight from 10,000 g/mol to 100,000 g/mol.

6. A mineral flotation composition according to claim 4, wherein said first depressant has a weight average molecular weight from 10,000 g/mol to 100,000 g/mol.

7. A mineral flotation composition according to claim 1, wherein X units of Formula (I) is greater than 50% and no Z units are present.

8. A mineral flotation composition according to claim 1, wherein $R^6$ is H, $R^7$ is $CH_2COO^-M^+$, and each $M^+$ in Formula (III) is K.

9. A mineral flotation composition according to claim 6, wherein $R^6$ is H, $R^7$ is $CH_2COO^-M^+$, and each $M^+$ in Formula (III) is K.

10. A mineral flotation composition according to any one of claims 1 and 6 to 9, wherein the blend of the first and second depressant further comprises, or is used in combination with, a value mineral enhancing amount of a surface modifying agent.

11. A mineral flotation composition according to claim 10, wherein the surface modifying agent is one or more compound selected from the group consisting of NaSH, NaCN, Nokes reagent, mercapto ethanol, thioglycolic acid or salts thereof (including sodium, potassium, calcium, magnesium, or aluminum salts), sodium ferrocyanides, potassium ferrocyanides, hydroxyethyl trithiocarbonates, carboxymethyl trithiocarbonates, sodium trithiocarbonates, hydrogen peroxide, ozone, air, oxygen, sulfur dioxide, zinc cyanide, calcium cyanide, arsenic Nokes, mercapto propionic acid, mercapto succinic acid, 2-thiouracil, and thioglycerol.

12. A mineral flotation composition according to claim 11, wherein the surface modifying agent is NaSH, Na2S, sodium salt of thioglycolic acid, or Nokes reagent and is present from 0.5 wt. % to 99.5 wt. %, based on the total weight of the blend.

13. A method for selectively separating value sulfide minerals from non-value sulfide minerals in a froth flotation process for the recovery of said value minerals from an ore or concentrate containing said value and non-value minerals, the method comprising:

adding to one or more stage of the froth flotation process a mineral flotation composition as defined by any one of claims 1, 4, 6 to 9, and 12; and recovering said value minerals from the froth.

14. A method according to claim 13, wherein a first and second depressant of the mineral flotation composition are added as a one pack blend.

15. A method according to claim 13, wherein the mineral flotation composition is as defined by claim 4.

16. A method according to claim 13 further comprising adding an effective amount of one or more flotation reagents selected from the group consisting of collectors, frothers, froth phase modifiers, dispersants, depressants, suppressants, pH regulators, and activators to one or more stages of said froth flotation process.

17. A method according to claim 13, wherein a first and second depressant of the mineral flotation composition are added together in a one pack blend in a dosage of from 2 kg/ton to 15 kg/ton of ore or concentrate.

18. A method according to claim 13, wherein a first and a second depressant of the mineral flotation composition are co-added, and wherein the dosage of the first depressant is from 0.5 kg/ton to 1.5 kg/ton of ore or concentrate, and the dosage of the second depressant is from 1.5 kg/ton to 25 kg/ton of ore or concentrate.

19. A method according to claim 13, wherein said value minerals are selected from the group consisting of sulfides of molybdenum, copper, zinc, nickel, lead, and mixtures thereof.

20. A method according to claim 19, wherein said value mineral is molybdenite and said non-value mineral is copper sulfides and/or iron sulfides.

\* \* \* \* \*